United States Patent [19]

Irving et al.

[11] Patent Number: 5,576,461
[45] Date of Patent: Nov. 19, 1996

[54] PREPARATION OF SULPHOXONIUM SALTS

[75] Inventors: Edward Irving, Higher Whitley; Robert J. Lunn, Bar Hill; David A. Taylor, Cambridge; Alan H. Haines, Taverham; John P. Innocenzi, Ashton, all of England

[73] Assignee: Ciba-Geigy Corporation, Tarrytown, N.Y.

[21] Appl. No.: 622,905

[22] Filed: Dec. 6, 1990

[30] Foreign Application Priority Data

Dec. 6, 1989 [GB] United Kingdom .................... 8927530

[51] Int. Cl.$^6$ ................................................. C07C 315/00
[52] U.S. Cl. ................. 568/27; 568/13; 568/14; 522/31; 556/69
[58] Field of Search .................... 522/31; 568/27, 568/13, 14; 556/69

[56] References Cited

U.S. PATENT DOCUMENTS

| | | | |
|---|---|---|---|
| 4,339,567 | 7/1982 | Green | 522/31 |
| 4,398,014 | 8/1983 | Green et al. | 522/31 |
| 4,628,087 | 12/1986 | Meneghin | 568/27 |

FOREIGN PATENT DOCUMENTS 1538890  9/1968  France .

OTHER PUBLICATIONS

House "Modern Synthetic Reactions", Second Ed. 1972 W.A. Benjamin, Inc. pp. 321–329.

*Primary Examiner*—Mark Chapman
*Attorney, Agent, or Firm*—William A. Teoli; Luther A. R. Hall

[57] ABSTRACT

The present invention provides a process for preparing a sulphoxonium salt from the corresponding sulphonium salt which comprises oxidising the sulphonium salt using a peracid, under basic conditions, in a solvent other than a ketone.

Some of the sulphoxonium salts are new compounds.

15 Claims, No Drawings

PREPARATION OF SULPHOXONIUM SALTS

The present invention relates to a process for making sulphoxonium salts some of which are new compounds.

Sulphoxonium salts have been described as initiators for the photopolymerisation of cationically polymerisable materials. Various methods for their preparation have been disclosed (see for example U.S. Pat. No. 4,339,567). One such method for triaryl sulphoxonium salts comprises oxidation of the corresponding triarylsulphonium salt with m-chloroperbenzoic acid in acetone solution.

We have now surprisingly found that the yield of sulphoxonium salt can be increased and the product is not contaminated with starting material, if the oxidation is carded out under basic conditions in a solvent other than a ketone.

Accordingly the present invention provides a process for preparing a triaryl sulphoxonium salt from the corresponding sulphonium salt which comprises oxidising the sulphonium salt using a peracid, under basic conditions, in a solvent other than a ketone.

The peracid may be added as such or formed in situ. It may be an aliphatic peracid, but is preferably an aromatic peracid. It may be a carboxylic or sulphonic peracid.

When generated in situ, it may be obtained by adding the carboxylic or sulphonic acid, or a derivative thereof such as a chloride or anhydride, together with an oxidising agent such as hydrogen peroxide, an alkali metal peroxide or superoxide, a perborate or percarbonate.

Examples of suitable peracids include m-chloroperoxybenzoic acid, monoperoxyphthalic acid magnesium salt, perbenzoic acid and peracids of p-toluene sulphonic acid, benzenesulphonic acid, trichloroacetic acid and trifluoroacetic acid.

A wide range of solvents may be used such as alcohols, e.g. methanol, ethanol or commercial alcoholic solvents such as industrial methylated spirits, nitriles e.g. acetonitrile, chlorinated hydrocarbons e.g. dichloromethane and heterocyclic compounds e.g. tetrahydrofuran. The preferred solvents are alcohols.

Basic conditions may be provided by adding a base such as an alkali metal hydroxide, alkoxide, carbonate or bicarbonate, e.g. sodium hydroxide, potassium carbonate, sodium methoxide, but preferably alkali metal hydroxides or carbonates, e.g. sodium hydroxide or potassium carbonate.

The peracid may be used in sufficient quantity to carry out the oxidation, but is preferably used in a small excess. The base is preferably present in at least equimolar amounts compared to the amount of peracid, but preferably a small excess is used.

The reaction may be carried out at temperatures from below 0° C. up to the reflux temperature of the reaction mixture, but ambient temperature is preferred.

The sulphoxonium salt is preferably of the general formula (I)

$$R^1R^2R^3S^+=O \ X^- \qquad (I)$$

where $R^1$, $R^2$ and $R^3$ are the same or different and each is an aryl group of 6 to 10 carbon atoms which is unsubstituted or substituted by one or more halogen atoms, hydroxy groups, nitro groups, amino groups, alkyl or alkoxy groups having 1 to 8 carbon atoms, aryl groups, aryloxy groups, aralkenyl groups or a group of the formula (II) or (III)

where $R^4$ is an arylene group derived from an $R^1$ group, n is an integer from 1 to 4, preferably 2, and $R^5$ is an aryl group as defined for $R^1$ to $R^3$; and $X^-$ is an anion.

Anion $X-$ may be a simple anion such as halogen, e.g. chloride or bromide, trifluoromethanesulphonate or preferably an ion of the formula (IV)

$$MY_m^- \qquad (IV)$$

where M is an atom of a metal or metalloid, Y is a halogen atom such as fluorine or chlorine and m is 4, 5 or 6 and is one more than the valency of M. M may be boron, bismuth, antimony, arsenic or phosphorus. Thus anion $X^-$ may be $BiCl_6^-$, $BF_4^-$, $PF_6^-$, $SbF_6^-$ or $AsF_6^-$.

Examples of aryl groups $R^1$, $R^2$ or $R^3$ include phenyl, tolyl, xylyl, mesityl, p-octylphenyl, biphenyl, naphthyl, stilbenyl, p-methoxyphenyl, p-hydroxyphenyl, p-phenoxyphenyl, p-chlorophenyl, p-bromophenyl, 2,4-dimethoxyphenyl, 2,4,6-trimethoxyphenyl, m-nitrophenyl, p-dimethylaminophenyl, the group

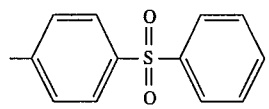

and the group

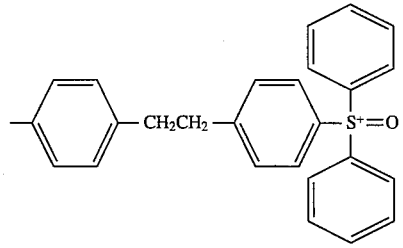

Preferably at least one of $R^1$, $R^2$ and $R^3$ is substituted.

Some of the sulphoxonium compounds of formula (I) are new and form another aspect of the present invention. The new compounds are those of formula (I) where at least one of $R^1$, $R^2$ and $R^3$ is substituted by hydroxy, amino, nitro, aryl, aryloxy, aralkenyl or a group of the formula II or III.

It should be noted that sulphoxonium salts with one anion can be easily converted into salts with a different anion by double conversion. For example a hexafluorophosphate can be made by reacting the corresponding sulphoxonium chloride with potassium hexafluorophosphate. In a similar way the starting sulphonium salt can also be made with a desired anion.

It is also possible to carry out reactions to introduce or change substitutents on an aryl ring in the sulphoxonium cation. For example ether cleavage of an alkoxy group will produce a hydroxy group substituent. This may be carded out for instance using hydriodic acid at elevated temperature. Nitro groups may be introduced by a nitration reaction using concentrated, preferably fuming nitric acid.

The sulphonium salts used as starting materials are either known or can be made by methods known per se e.g. as described by Crivello and Lam, J. Polymer Sci., Polymer Chemistry: 1980, 18, 2697–2714; or by Endo, Shudo and Okamoto, Chem. Pharm. Bull: 1981, 29, (12), 3753–3755.

The sulphoxonium salts obtained according to the present invention are useful as cationic photoinitiators for cationically polymerisable materials. They may be used in amounts of 0.1 to 7.5, preferably 0.5 to 5.0 parts by weight per 100 parts by weight of polymerisable material.

The sulphoxonium salts may be used alone or together with a sensitiser to increase the speed of curing. Suitable sensitisers include dyes or aromatic polycyclic compounds such as anthracene, 9-methylanthracene, rubrene, perylene, acenaphthene, phenanthrene, fluoroanthene and pyrene. Other suitable sensitisers are disclosed in U.S. Pat. No. 4,069,054.

A wide range of cationically polymerisable materials may be photopolymerised using sulphoxonium salts obtained by the present invention e.g. those described in U.S. Pat. No. 4,339,567 including epoxides, vinyl compounds, aminoplasts and phenoplasts. Preferred compounds are aromatic glycidyl ethers, especially aromatic diglycidyl ethers.

The invention is illustrated by the following Examples.

In the Examples, IR spectra were obtained using a KBr disc for solid products and a liquid film for liquids; nmr data were obtained using a machine with a spectral frequency of 250 MHz and using $d_6$ acetone.

EXAMPLE 1

Triphenylsulphonium hexafluorophosphate (75 g, 177 mmole) is suspended in methanol (1250 ml) and potassium carbonate (152 g, 1.1 mole) is added. The stirred suspension is cooled to 0° C. and m-chloroperoxybenzoic acid (159 g, 0.92 mole) is added. The suspension is stirred at 0° C. for 7 hours and then at room temperature for 3 days. 1M aqueous sodium thiosulphate solution (920 ml) is added to reduce the oxidizing species. The methanol is removed under reduced pressure and a white precipitate forms. This is collected, washed with water and diethyl ether and dried in vacuo at 50° C. Yield 61.2 g, 79%, mp 260°–261° C.

IR: 1455, 1225, 1080, 840, 755, 730, 680 cm$^{-1}$: 8.04 (m,6H), 8.16 (m, 9H) ppm

EXAMPLES 2 to 12

Following the procedure of Example 1 using the appropriate sulphonium salt, the following sulphoxonium salts are prepared.

| Example | Salt | Yield (%) | m.p. (°C.) |
|---|---|---|---|
| 2 | 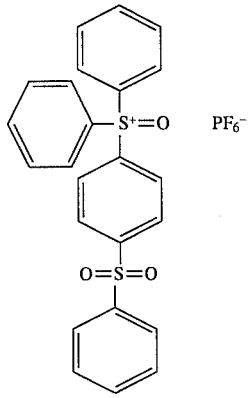 | 95 | oil |

IR: 1580, 1440, 1305, 1150, 1080, 840, 730 cm$^{-1}$
δ: 7.09(t, J=9Hz), 7.44–7.70(m), 7.90–8.20(m)ppm

| | | | |
|---|---|---|---|
| 3 | 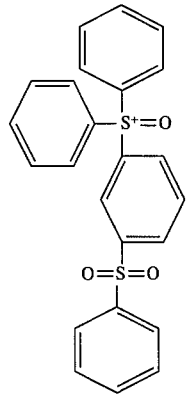 | 57 | 121–123 |

IR: 1575, 1440, 1305, 1150, 1075, 840, 725, 680 cm$^{-1}$
δ: 7.52–8.74(m)ppm

-continued
| Example | Salt | Yield (%) | m.p. (°C.) |
|---|---|---|---|
| 4 | 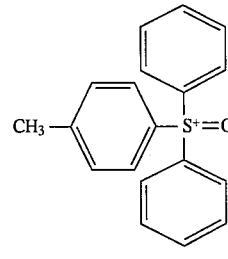 | 75 | 170–172 |
IR: 1600, 1440, 1230, 1090, 850, 740, 710, 680 cm$^{-1}$
δ: 2.60(s, 3H), 7.81(d, J=9Hz, 2H), 8.00(m, 6H), 8.16(m, 6H)ppm
| 5 | 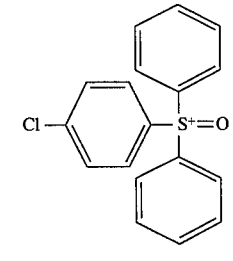 | 40 | 81–83 |
IR: 1590, 1450, 1315, 1090, 840, 765, 735, 690 cm$^{-1}$
δ: 7.64(m, 6H), 7.90–8.20(m, 8H), ppm
| 6 | 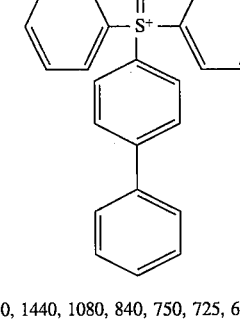 | 90 | oil |
IR: 1580, 1440, 1080, 840, 750, 725, 695, 670 cm$^{-1}$
δ: 7.35–8.25(m, 19H), ppm
| 7 | 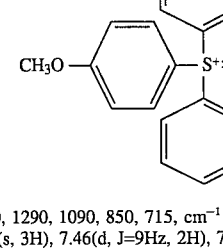 | 68 | 157–159 |
IR: 1600, 1290, 1090, 850, 715, cm$^{-1}$
δ: 4.05(s, 3H), 7.46(d, J=9Hz, 2H), 7.95–8.20(m, 14H), ppm
| 8 | 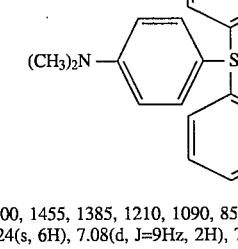 | 58 | 216–218 |
IR: 1600, 1455, 1385, 1210, 1090, 850, 760, 740, 710, 690, 645, cm$^{-1}$
δ: 3.24(s, 6H), 7.08(d, J=9Hz, 2H), 7.63(d, J=9Hz, 2H), 7.97(m, 4H), 8.10

| Example | Salt | Yield (%) | m.p. (°C.) |
|---|---|---|---|
| | (m, 6H), ppm | | |
| 9 | 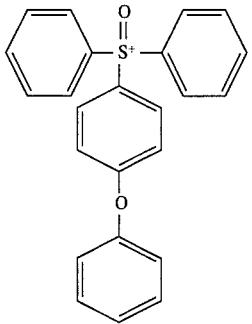 PF$_6^-$ | 80 | oil |
| | IR: 1580, 1260, 1080, 840, 750, 725, 705, 675, cm$^{-1}$<br>δ: 6.80–8.20(m, 19H), ppm | | |
| 10 | 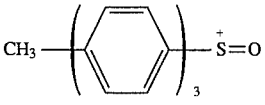 PF$_6^-$ | 90 | semi-solid |
| | IR: 1580, 1080, 840, 690, 660, cm$^{-1}$<br>δ: 2.58(s, 9H), 7.81(m, 6H), 7.96(m, 6H)ppm | | |
| 11 | 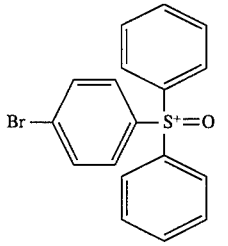 PF$_6^-$ | 40 | oil |
| | IR: 1580, 1440, 1080, 840, 720, 670, cm$^{-1}$<br>δ: 7.50–8.20(m, 14H)ppm | | |
| 12 | 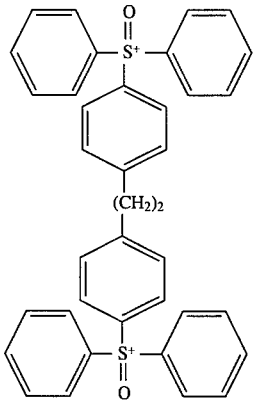 PF$_6^-$ ... PF$_6^-$ | 73 | semi-solid |
| | IR: 1590, 1450, 1080, 840, 755, 730, 710, 680, 635, cm$^{-1}$<br>δ: 3.00(br, 4H), 7.83(d, J=9Hz, 4H), 8.00(12H, m), 8.14(12H, m)ppm | | |

| Example | Salt | Yield (%) | m.p. (°C.) |
|---|---|---|---|
| 13 | 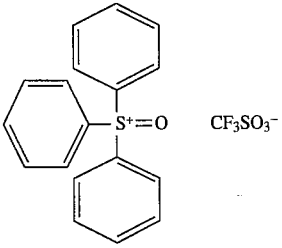 Ph₃S⁺=O  CF₃SO₃⁻ | 60 | 213–4 |

IR: 1450, 1270, 1225, 1160, 1080, 1035, 770, 685, 640 cm⁻¹
δ: 8.00(m, 6H), 8.20(m, 9H)ppm

EXAMPLE 14

Triphenylsulphonium hexafluorophosphate (0.5 g, 1.23 mmole) is dissolved in methanol (40 ml) and cooled to 0° C. Potassium carbonate (2.15 g, 15.6 mmole) is added followed by monoperoxyphthalic acid magnesium salt (1.52 g, 3.08 mmole). The suspension is stirred at 0° C. for 7 hours and then at room temperature for 2 days during which time the suspension thickens and stirring is ceased. 2M aqueous hydrochloric acid is added to take the pH of the suspension to 5 followed by 1M aqueous sodium thiosulphate until no oxidizing species are present. The methanol is removed under reduced pressure and the white precipitate is collected, washed with water and diethyl ether and finally dried in vacuo at 50° C. Yield 0.25 g, 48%, m.p. 259°–260° C.

EXAMPLES 15 to 17

Following the procedure of Example 14 using the appropriate sulphonium salt, the following sulphoxonium salts are prepared.

| Example | Salt | Yield (%) | m.p. (°C.) |
|---|---|---|---|
| 15 | C₈H₁₇—C₆H₄—S⁺(=O)(Ph)₂  PF₆⁻ | 46 | wax |

IR: 1585, 1080, 840, 750, 730, 680 cm⁻¹
δ: 0.85(m, 2H), 1.23(m, 10H), 1.66(m, 1H), 2.85(m, 4H), 7.40–8.20 (m, 14H)ppm

| 16 | CH₃—C₆H₄—S⁺(=O)(Ph)₂  AsF₆⁻ | 51 | 155–157 |

IR: 1230, 1085, 850, 760, 730, 705 cm⁻¹
δ: 2.61(s, 3H), 7.82(d, J=9Hz, 2H), 8.02(m, 6H), 8.18(m, 6H)ppm

| Example | Salt | Yield (%) | m.p. (°C.) |
|---------|------|-----------|------------|
| 17 | 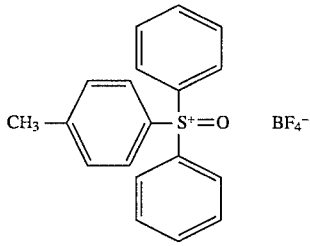 | 61 | 131–133 |

IR: 1585, 1450, 1220, 1080, 1050, 760, 730, 705, 680 cm$^{-1}$
δ: 2.60(s, 3H), 7.81(d, J=9Hz, 2H), 8.00(m, 6H), 8.15(m, 6H)ppm

EXAMPLE 18

Triphenylsulphonium hexafluorophosphate (0.5 g, 1.23 mmol) is dissolved with stirring at room temperature in ethanol (20 ml). 10 ml of a solution of saturated potassium carbonate solution are added, and the two-phase mixture stirred whilst solid monoperoxyphthalic acid magnesium salt hydrate (1.52 g, 3.08 mmol) is added. The mixture is stirred for 5 hours before working up as in Example 1 to given an off-white powder (0.24 g, 46%) m.p. 256°–257° C.

EXAMPLE 19

Triphenylsulphonium hexafluorophosphate (0.5 g, 1.23 mmol) is dissolved in methanol (20 ml) and potassium carbonate (2.15 g, 15.6 mmol) is added. The resulting suspension is stirred at room temperature while a solution of monoperoxyphthalic acid magnesium salt hydrate (1.52 g, 3.08 mmol) in methanol (10 ml) is added dropwise over 2 hours.

After a total of 5 hours the reaction is worked up as in Example 14 to give a white solid 0.41 g, 79% with m.p. 258°–260° C.

EXAMPLE 20

Example 14 is repeated but at room temperature and after 5 hours the reaction is worked up to give product 0.3 g (58%) with m.p. 258°–260° C.

EXAMPLE 21

Example 14 is repeated but at 8°–9° C. and after 5 hours the reaction is worked up to give product 0.28 g (54%) with m.p. 259°–261° C.

EXAMPLE 22

Example 14 is repeated but using industrial methylated spirits solvent (20 ml); giving product 0.31 g (60%) with m.p. 256°–258° C.

EXAMPLE 23

Triphenylsulphonium hexafluorophosphate (2.5 g, 6.15 mmol) is dissolved in industrial methylated spirits (50 ml) and stirred at room temperature with saturated potassium carbonate solution (30 ml) in a two-phase system. A solution of monoperoxyphthalic acid magnesium salt hydrate (7.6 g, 15.4 mmol) is added dropwise over one and half hours. After a total of 5 hours the reaction mixture is filtered. The solid collected is washed with dilute hydrochloric acid, water and ether to give 1.36 g of a white solid m.p. 263°–4° C. The filtrate is worked up as in Example 1 to give a white solid 0.17 g m.p. 263°–264° C. Combined yield 59%.

EXAMPLE 24

Triphenylsulphonium hexafluorophosphate (10.5 g, 0.026 mmol) and p-toluenesulphonyl chloride (29.4 g, 0.15 mol) are dissolved in methanol (310 ml) with stirring at room temperature. A solution of hydrogen peroxide (30%, 32 ml, 0.28 mol) and sodium hydroxide (24.7 g, 0.62 mol) in water (210 ml) is added slowly over 45 min causing an exotherm to ca. 45° C.

After one hour, methanol is distilled off under reduced pressure and the resulting precipitate is washed with water and ether to give triphenylsulphoxonium hexafluorophosphate (10.38 g, 95%) as a beige solid with spectra identical to those of authentic material.

EXAMPLE 25

(Tolyl)diphenylsulphonium hexafluorophosphate (1.08 g, 2.57 mmol) is dissolved with stirring in methanol (40 ml). The resulting solution is cooled in an icewater bath while solid potassium superoxide (2.20 g, 31 mmol) is added slowly (with evolution of oxygen). After stirring for a further 15 minutes, a solution of p-toluenesulphonyl chloride (2.38 g, 12.5 mmol) in 30 ml methanol is added dropwise over 20–30 minutes. The reaction mixture is stirred for a further 30 min. After this time the mixture is filtered under vacuum. The residue is washed with methanol and the combined filtrate evaporated under reduced pressure. The resulting solid is slurried with water, filtered, and washed with water and ether, to give (tolyl)diphenylsulphoxonium hexafluorophosphate (0.6 g, 54 %) identical with authentic material.

EXAMPLE 26

(Tolyl)diphenylsulphonium hexafluorophosphate (1.08 g, 2.57 mmol) is dissolved with stirring in methanol (40 ml). The reaction mixture is cooled in an ice-water bath while sodium peroxide (2.42 g, 31 mmol) is added slowly. After 15 minutes, p-toluenesulphonyl chloride (2.38 g, 12.5 mmol) in 30 ml methanol is added dropwise over 20 minutes. After a further 1 hour the mixture is filtered under vacuum. The residue is washed with methanol and the combined filtrate evaporated in vacuo. Water is added and the product collected by filtration and washed with water and then ether. The resultant (tolyl)diphenylsulphoxonium hexafluorophosphate (0.35 g, 31%) was identical with authentic material.

EXAMPLE 27

A reaction exactly as in Example 26, but carded out in industrial methylated spirits instead of methanol gives the sulphoxonium salt (1.11 g, 99%).

EXAMPLE 28

Benzenesulphonyl chloride (2.20 g, 0.0125 mol) in methanol (30 ml) is added dropwise over 20 minutes to an ice-cooled mixture of potassium superoxide (2.20 g, 0.031 mol), triphenylsulphonium hexafluorophosphate (1.05 g, 0.00257 mol) and methanol (40 ml). After 30 minutes the mixture is filtered and the filtrate evaporated in vacuo to ca. 5 ml, affording a white precipitate. This is collected and washed with water to give a solid (0.735 g). A further 0.2 g is obtained by trituration of the residue from filtration in dichloromethane, filtering, and concentration in vacuo. Total yield of triphenylsulphoxonium hexafluorophosphate is 0.935 g (86%).

EXAMPLE 29

(Tolyl)diphenylsulphonium hexafluorophosphate (1.08 g, 2.57 mol) is dissolved in methanol (40 ml) with cooling in an ice-water bath. Sodium peroxide (2.42 g, 31 mmol) is added slowly. After 15 mins a solution of trichloro- acetyl chloride (1.4 ml, 12.5 mol) in methanol (30 ml) is added over 20 mins. After a further 30 mins the reaction mixture is filtered under vacuum and the filtrate evaporated in vacuo. Water is added and the resulting solid collected, washed with water and ether to give (tolyl)diphenylsulphoxonium hexafluorophosphate (0.72 g, 64%) with spectra identical to those of authentic material.

EXAMPLE 30

(Tolyl)diphenylsulphonium hexafluorophosphate (1.08 g, 2.57 mol) and p-toluenesulphonyl chloride (2.38 g, 12.5 mmol) are dissolved with stirring in methanol (40 ml) with cooling in ice water. Sodium methoxide (1.67 g, 31 mmol) and hydrogen peroxide (30% in water, 3.5 g, 31 mmol) are added over 25 mins. After 1 hour the reaction mixture is filtered and evaporated in vacuo. Water is added and the resulting solid is collected and washed with water and ether to give (tolyl)diphenylsulphoxonium hexafluorophosphate (1.08 g, 96%) with spectra identical to those of authentic material.

EXAMPLE 31

(Tolyl)diphenylsulphonium hexafluorophosphate (1.08 g, 2.57 mol) is dissolved with stirring in methanol (40 ml) with cooling in an ice-water bath. Sodium methoxide (2.42 g, 31 mmol) is added slowly. After 15 mins a solution of trifluoroacetic anhydride (1.8 ml, 12.5 mmol) in methanol (30 ml) is added dropwise over 25 min. After 30 min the reaction mixture is filtered and evaporated under reduced pressure. Water is added and the resulting solid is collected and washed with water and ether, to give (tolyl)diphenylsulphoxonium hexafluorophosphate (0.85 g, 76%) identical to authentic material.

EXAMPLE 32

(Tolyl)diphenylsulphonium hexafluorophosphate (1.08 g, 2.57 mol) is dissolved with stirring in methanol (40 ml) with cooling in ice-water. p-Toluenesulphonyl chloride (2.38 g, 12.5 mmol) is added slowly. After 15 mins a solution of hydrogen peroxide (30% in water, 3.5 g, 31 mmol) and sodium hydroxide (1.24 g, 31 mmol) in water (25 ml) is added dropwise over 10 min. After a further one and a half hours the reaction mixture is filtered and evaporated in vacuo. Water is added and the resulting solid is collected and washed with water and ether, to give (tolyl)diphenylsulphoxonium hexafluorophosphate (0.88 g, 79%) identical to authentic material.

EXAMPLE 33

(Tolyl)diphenylsulphonium hexafluorophosphate (1.08 g, 2.57 mol) and sodium methoxide (1.67 g, 31 mmol) are dissolved with stirring in methanol (40 ml). The resulting solution is cooled in an ice-water bath while urea-hydrogen peroxide complex (1:1, 2.91 g, 31 mmol) is added slowly. After 15 mins a solution of p-toluenesulphonyl chloride (2.38 g, 12.5 mmol) in methanol (30 ml) is added dropwise over 20 min. After a futher 1 hour the reaction mixture is filtered and evaporated under reduced pressure. Water is added and the resulting solid collected, and washed with water and ether. The resultant (tolyl)diphenylsulphoxonium hexafluorophosphate (0.53 g, 47%) is identical to authentic material.

EXAMPLE 34

(Tolyl)diphenylsulphonium hexafluorophosphate (1.08 g, 2.57 mmol) and p-toluenesulphonyl chloride (2.38 g, 12.5 mmol) are dissolved with stirring in methanol (40 ml). The resulting solution is stirred in an ice-water bath while a solution of sodium percarbonate (4.87 g, 31 mmol) in water (30 ml) is added over 15 min. After 30 min the reaction mixture is filtered and evaporated under reduced pressure. Water is added and the resulting solid collected, and washed with water and ether. The resulting slightly damp (tolyl)diphenylsulphoxonium hexafluorophosphate (1.21 g) is identical to authentic material.

EXAMPLE 35

(Tolyl)diphenylsulphonium hexafluorophosphate (1.08 g, 2.57 mmol) and p-toluenesulphonyl chloride 2.38 g, 12.5 mmol are dissolved in methanol (40 ml) with stirring in an ice-water bath. A solution of sodium carbonate (3.29 g, 31 mmol) and hydrogen peroxide (30% in water, 3.5 g, 31 mmol) in water (30 ml) is added dropwise over 20 mins. After a further 30 min the reaction mixture is filtered and evaporated in vacuo. Water is added and the resulting solid collected and washed with water and ether. The resultant (tolyl)diphenyl- sulphoxonium hexafluorophosphate (1.06 g, 95%) is identical to authentic material.

EXAMPLE 36

(p-Methoxyphenyl)diphenylsulphonium hexafluorophosphate (5.6 g, 12.8 mmol) and p-toluenesulphonyl chloride (6.1 g, 32 mmol) are dissolved in methanol (300 ml) with stirring at 15° C.

A solution of sodium hydroxide (5.1 g, 0.31 mmol) and hydrogen peroxide (30% in water, 6.7 g, 60 mmol) in water (50 ml) is added dropwise. The reaction mixture is stirred, and allowed to reach room temperature overnight. Methanol is removed in vacuo to give a white granular solid. After collection and washing with water and ether (p-methoxyphenyl)diphenyl- sulphoxonium hexafluorophosphate (4.9 g, 84%) is obtained identical to authentic material.

EXAMPLE 37

Triphenylsulphonium hexafluoro-phosphate (1.05 g, 2.57 mmol) and p-toluenesulphonyl chloride (0.73 g, 3.9 mmol) are dissolved with stirring in methanol (35 ml) at room temperature. A solution of sodium peroxide (0.5 g, 6.4 mmol) in water (30 ml) is added dropwise over 30 min. After 2 hours water is added and the white solid collected, washed with water and ether. The resulting triphenylsulphoxonium hexafluorophosphate (0.56 g, 52%) is identical to authentic material.

EXAMPLE 38

(Tolyl)diphenylsulphonium hexafluorophosphate (1.08 g, 2.57 mmol) and p-toluenesulphonyl chloride 2.38 g, 12.5 mmol are dissolved with stirring in tetrahydrofuran (40 ml). A solution of sodium peroxide (2.42 g, 31 mmol) in water (30 ml) is added dropwise over 25 minutes. After a further hour the reaction mixture is filtered and evaporated under reduced pressure. Water is added and the resulting solid collected, and washed with water and ether. The resulting white solid (1.06 g, 95%) has spectra identical to those of authentic material.

EXAMPLE 39

Triphenylsulphoxonium hexafluorophosphate (1 g, 2.36 mmol) is dissolved in concentrated $H_2SO_4$ (10 ml) and is kept at 15° C. in a water bath. Then fuming nitric acid (1.1 equiv. 0.18 g, 0.12 ml) is added. The stirred solution is heated at 80°–90° C. for 6 hours. It is allowed to cool and is poured into aqueous potassium hexafluorophosphate solution. The yellow precipitate is collected and washed with water until the washings are neutral. The filter cake is then washed with diethyl ether and dried in vacuo at 40° C. Yield of the mononitrated product is 1 g, 91%, m.p. 93°–96° C.

IR: 1530, 1350, 1225, 1075, 840, 725 $cm^{-1}$: 8.00–9.00 (m,14H) ppm

EXAMPLE 40

(4-Methoxyphenyl)diphenylsulphoxonium hexafluorophosphate (3 g, 6.6 mmol) is stirred at 120°–125° C. in hydriodic acid (57% in water, 15 ml) for 4 hours. It is allowed to cool and is poured into potassium hexafluorophosphate solution. The precipitate is collected and found to be (4-hydroxyphenyl)diphenylsulphoxonium hexafluorophosphate, yield 20% m.p. 200°–202° C.

IR: 3200, 1580, 1080, 840, 755,730, 710, 680 $cm^{-1}$: 7.35 (d,J=9 Hz,2H), 7.98 (m,6H), 8.16 (m,6H), 10.75 (br,1H) ppm

EXAMPLE 41

Example 39 is repeated but using 5 equivalents of nitric acid. The yield of tris(m-nitrophenyl)sulphoxonium hexafluorophosphate is 74%, m.p. 135°–139° C.

IR: 1600, 1540, 1355, 845,730, 660 $cm^{-1}$: 8.00–9.20 (m,12H) ppm

EXAMPLE 42

(Tolyl)diphenylsulphonium hexafluorophosphate (1.08 g, 2.57 mmol) is dissolved with stirring in acetonitrile (40 ml). The resulting solution is stirred while p-toluene- sulphonyl chloride (2.38 g, 12.5 mmol) added. The reaction mixture is cooled in an ice-water bath. A solution of sodium peroxide (2.42 g, 31 mmol) in water (30 ml) is added dropwise over 20 minutes. After a further 2 hours the reaction mixture is filtered under vacuum and the filtrate evaporated in vacuo. Water is added and the resulting solid collected, and washed with water and ether to give (tolyl)diphenylsulphoxonium hexafluorophosphate (0.63 g, 56%) with spectra identical to authentic material.

EXAMPLE 43

(Tolyl)diphenylsulphonium hexafluorophosphate (1.08 g, 2.57 mmol) and p-toluenesulphonyl chloride (2.38 g, 12.5 mmol) are dissolved with stirring in dichloromethane (40 ml), with cooling in ice-water. A solution of sodium peroxide (2.42 g, 31 mmol) in water (30 ml) is added dropwise over 20 minutes. After further stirring overnight the reaction mixture is diluted with dichloromethane and water. The mixture is allowed to separate and the dichloromethane containing layer collected, dried over magnesium sulphate, filtered and evaporated in vacuo. The resulting solid is slurried in water and collected. It is further washed with water and ether to yield (tolyl)diphenylsulphoxonium hexafluorophosphate (0.73 g, 65%) identical to authentic material.

EXAMPLES 44–48

Compositions comprising 2,2-bis(p-glycidyloxyphenyl) propane (100 parts by weight) a sulphoxonium salt as indicated in the Table below (3 parts by weight) with and without 1 part by weight of 9-methyl- anthracene as sensitiser, are applied as a film 24 μm thick on tinplate. They are then exposed in two ways to produce a tack free coating. The first is simple exposure to a metal halide lamp (5000 w) at a distance of 75 cm and the time taken to become tack-free is recorded. The second is to expose the film to radiation from a medium pressure mercury arc lamp (80 W per cm) at a distance of 8 cm on a Primarc type apparatus running at 21.3 m/min. The number of passes needed for a tack-free coating is recorded.

| Example | Salt from Example | Time | with sensitiser | No. of Passes | with sensitiser |
| --- | --- | --- | --- | --- | --- |
| 44 | 2 | 7.5 min | 15 sec | 6 | 5 |
| 45 | 6 | 1 min | 8 sec | 3 | 2 |
| 46 | 9 | 3.3 min | 15 sec | 5 | 4 |
| 47 | 12 | 4.25 min | 25 sec | 9 | 5 |
| 48 | 36 | 2 min | 6 sec | 3 | 2 |
| 49 | 38 | 2.5 min | 6 sec | 2/3 | 2 |

EXAMPLES 50–55

The procedure of Examples 44–49 is repeated using, as the resin, 3,4-epoxycyclohexylmethyl 3',4'-epoxy cyclohexane carboxylate. The following results are obtained.

| Example | Salt from Example | Time | with sensitiser | No. of Passes | with sensitiser |
| --- | --- | --- | --- | --- | --- |
| 50 | 2 | >10 min | 40 sec | 2/3 | 1/2 |
| 51 | 6 | 3.5 min | 12 sec | 2/3 | 1/2 |
| 52 | 9 | 10 min | 13 sec | 2/3 | 2 |

-continued

| Example | Salt from Example | Time >10 min | with sensitiser | No. of Passes | with sensitiser |
|---------|-------------------|--------------|-----------------|---------------|-----------------|
| 53 | 12 | >10 min | 45 sec | 3/4 | 2/3 |
| 54 | 36 | >10 min | 14 sec | 3 | 2 |
| 55 | 38 | >10 min | 7 sec | 2/3 | 2 |

We claim:

1. A process for preparing a triaryl sulphoxonium salt from the corresponding sulphonium salt which comprises
    oxidizing the sulphonium salt using a peracid, under basic conditions, in a solvent other than a ketone which is an alcohol, chlorinated hydrocarbon or heterocyclic compound.

2. A process as claimed in claim 1 in which the peracid is an aliphatic or aromatic carboxylic or sulphonic peracid.

3. A process as claimed in claim 1 in which the peracid is added as such or is formed in situ.

4. A process as claimed in claim 1 in which the solvent is methanol, ethanol, industrial methylated spirits, dichloromethane or tetrahydrofuran.

5. A process as claimed in claim 1 in which the basic conditions are formed by an alkali metal hydroxide, alkoxide, carbonate or bicarbonate.

6. A process as claimed in claim 1 which is carried out at a temperature from below 0° C. up to the reflux temperature of the reaction mixture.

7. A process as claimed in claim 1 in which the sulphoxonium salt has the general formula (I)

$$R^1R^2R_3S^+=O \quad X^- \qquad (I)$$

where $R^1$, $R^2$ and $R^3$ are the same or different and each is an aryl group of 6 to 10 carbon atoms which is unsubstituted or substituted by one or more halogen atoms, amino groups, alkyl or alkoxy groups having 1 to 8 carbon atoms, aryl groups, aryloxy groups or a group of the formula (II) or (III)

$$-CH_2)_nR^4S^+=O \quad \begin{array}{c} R^2 \\ | \\ | \\ R^3 \end{array} \qquad (II)$$

$$\begin{array}{c} O \\ || \\ -S-R^5 \\ || \\ O \end{array} \qquad (III)$$

where $R^4$ is an arylene group derived from an $R^1$ group, n is an integer from 1 to 4, and $R^5$ is an aryl group as defined for $R^1$ to $R^3$; and $X^-$ is an anion.

8. A process as claimed in claim 7 in which $R^1$, $R^2$ and $R^3$ are selected from phenyl, tolyl, xylyl, mesityl, p-octylphenyl; biphenyl, naphthyl, stilbenyl, p-methoxyphenyl, p-hydroxyphenyl, p-phenoxyphenyl, p-chlorophenyl, p-bromophenyl, 2,4-dimethoxyphenyl, 2,4,6-trimethoxyphenyl, m-nitrophenyl, p-dimethylaminophenyl, the group

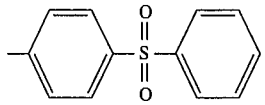

and the group

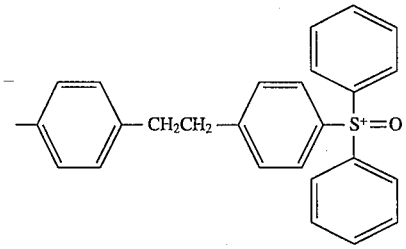

9. A process as claimed in claim 8 in which at least one of $R^1$, $R^2$ and $R^3$ is substituted.

10. A process as claimed in claim 8 in which the formed sulphoxnium salt is converted into another sulphoxonium salt.

11. A process as claimed in claim 10 in which a sulphoxonium salt containing an alkoxy group is converted into one containing a hydroxy group by reaction with hydroiodic acid at elevated temperature.

12. A process as claimed in claim 10 in which one or more nitro groups are introduced into a sulphoxonium ion by reaction with concentrated nitric acid.

13. A process as claimed in claim 10 in which a sulphoxonium salt with one anion is converted into a sulphoxonium salt with a different anion by double conversion.

14. A process as claimed in claim 7 in which anion $X^-$ is halogen, trifluoromethanesulphonate or an ion of the formula IV $$MY_m^- \qquad (IV)$$

where M is an atom of a metal or metalloid, Y is a halogen atom and m is 4, 5 or 6 and is one more than the valency of M.

15. A process as claimed in claim 14 in which anion $X^-$ is $BiCl_6^-$, $BF_4^-$, $PF_6^-$, $SbF_6^-$ or $AsF_6^-$.

* * * * *